United States Patent [19]

Kato et al.

[11] Patent Number: 4,578,174
[45] Date of Patent: Mar. 25, 1986

[54] OXYGEN SENSOR WITH HEATER

[75] Inventors: Nobuhide Kato, Ama; Takao Murase, Konan, both of Japan

[73] Assignee: NGK Insulators, Ltd., Japan

[21] Appl. No.: 604,973

[22] Filed: Apr. 27, 1984

[30] Foreign Application Priority Data

| May 9, 1983 | [JP] | Japan | 58-68661[U] |
| May 9, 1983 | [JP] | Japan | 58-68662[U] |
| May 9, 1983 | [JP] | Japan | 58-68666[U] |
| May 9, 1983 | [JP] | Japan | 58-68667[U] |

[51] Int. Cl.⁴ ............................................. G01N 27/58
[52] U.S. Cl. ..................................... 204/429; 209/427; 209/428
[58] Field of Search .................. 204/13, 421, 424–429

[56] References Cited

U.S. PATENT DOCUMENTS

| 3,654,112 | 4/1972 | Beekman's et al. | 204/427 |
| 4,107,019 | 8/1978 | Takao et al. | 204/425 |
| 4,129,491 | 12/1978 | Obiaya | 204/428 |
| 4,157,948 | 6/1979 | Maurer | 204/429 |
| 4,175,019 | 11/1979 | Murphy | 204/426 |
| 4,212,720 | 7/1980 | Maurer et al. | 204/424 |
| 4,282,080 | 8/1981 | Muller et al. | 204/427 |
| 4,300,990 | 11/1981 | Maurer | 204/427 |
| 4,304,652 | 12/1981 | Chiba et al. | 204/425 |
| 4,383,906 | 5/1983 | Sano et al. | 204/424 |
| 4,400,260 | 8/1983 | Stahl et al. | 204/427 |
| 4,407,704 | 10/1983 | Mase et al. | 204/428 |
| 4,419,213 | 12/1983 | Oshima et al. | 204/425 |
| 4,437,971 | 3/1984 | Csanitz et al. | 204/427 |
| 4,452,687 | 6/1984 | Torisu et al. | 204/427 |

Primary Examiner—John F. Niebling
Assistant Examiner—Terryence Chapman
Attorney, Agent, or Firm—Parkhurst & Oliff

[57] ABSTRACT

An oxygen sensor having a bar-shaped heater inserted in an elongate bore formed in a tubular solid electrolyte body which has porous platinum electrodes on its inner and outer surfaces and which is supported by a housing such that its closed end portion is exposed to exhaust gas and such that the elongate bore is gas-tight with respect to the exhaust gas. The bar-shaped heater comprises a heating resistor having a positive temperature coefficient, and a ceramic boyd carrying the heating resistor so as to embed the latter.

15 Claims, 14 Drawing Figures

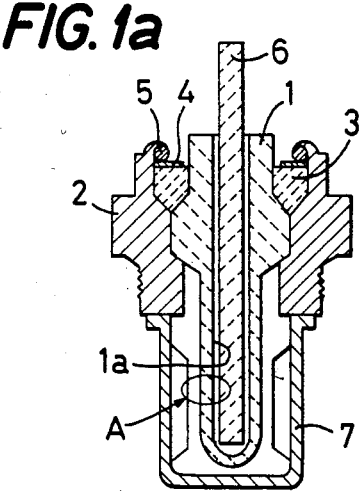
FIG. 1a
FIG. 1b
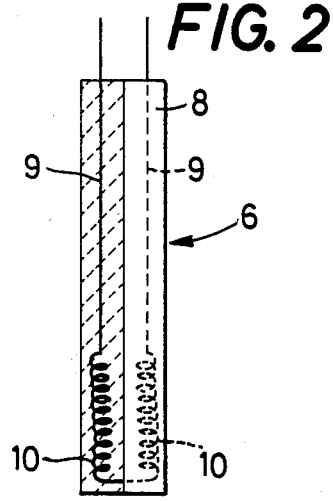
FIG. 2
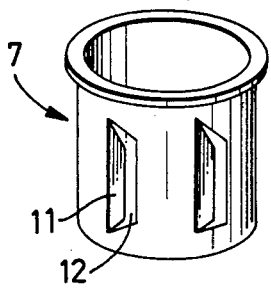
FIG. 3
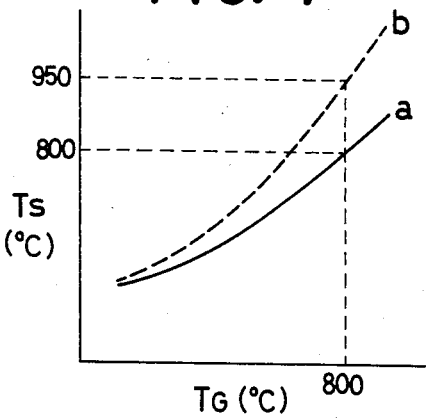
FIG. 4
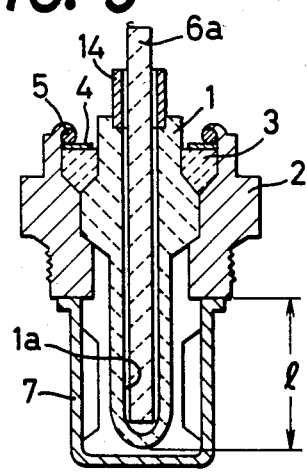
FIG. 5
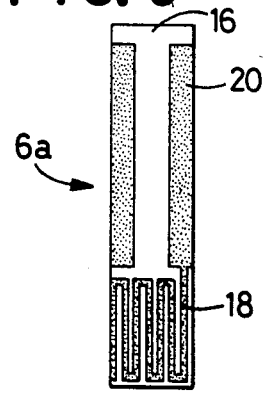
FIG. 6

OXYGEN SENSOR WITH HEATER

BACKGROUND OF THE INVENTION

The present invention relates generally to an oxygen sensor for detecting concentration of oxygen contained in exhaust gas emitted from an internal combustion engine. More particularly, the invention is concerned with such an oxygen sensor having a bar-shaped heater disposed in an elongate bore formed in a tubular solid electrolyte body.

In the art of controlling an air-fuel (A/F) ratio of an internal combustion engine for an automotive vehicle or for other applications, it is known to use an oxygen sensor which employs a mass of zirconia or other solid oxygen-ion conductive electrolyte to detect a content or concentration of oxygen in exhaust gas produced by the engine, according to the principle of an oxygen concentration cell. For example, such an oxygen sensor uses a solid electrolyte body of zirconia which is provided on its inner and outer surfaces with porous platinum electrodes, respectively. The electrode on the inner surface which defines an inner elongate bore in the zirconia body, is exposed to an ambient atmosphere and serves as a reference electrode (anode) which is exposed to a reference gas whose oxygen concentration is known. On the other hand, the electrode provided on the outer surface of the zirconia body is exposed to exhaust gas to be measured, so that this electrode serves as a measuring electrode (cathode) to monitor oxygen content of the exhaust gas. This oxygen sensor measures the oxygen concentration in the exhaust gas by measuring an electromotive force which is induced in response to a difference in the oxygen concentration between the reference and measuring electrodes.

However, the induced electromotive force is unstable until the solid electrolyte has been heated to a given point. Thus, the above type of oxygen sensor suffers a drawback that it is incapable of effecting an accurate control of an air-fuel ratio of the engine while the temperature of the exhaust gas of the engine is relatively low, for example while the engine is idling or immediately after the engine is started in its cold condition.

To solve such a drawback experienced in the art, it has been proposed to positively heat a solid electrolyte body by inserting a heater into an elongate cylindrical hole formed in the electrolyte body. For instance, Japanese Patent application laid open in 1979 under Publication No. 54-13396 discloses a heater which consists of an insulator bar and a heating wire (resistance wire) wound on the surface of the insulator bar. Further, Japanese Patent application laid open in the same year under Publication No. 54-22894 shows a so-called sheathed heater which uses a resistance coil wire disposed in a metal sleeve which is filled with a powdered electrically insulating material of high thermal conductivity so as to secure the coil wire in the metal sleeve.

Such proposed oxygen sensors equipped with a heater are disadvantageous in that their solid electrolyte is susceptible to excessive heat when the temperature of the exhaust gas of an internal combustion engine is elevated, whereby the porous platinum electrodes tend to be sintered with a result of reducing a rate of reaction of the measuring electrode to the exhaust gas, or a spinel coating layer protecting the electrodes tends to crack or flake off. Further, the heater is subject to an excessively high temperature due to a combined effect of its self-heating and exposure to heat of the exhaust gas, thereby suffering breakage of its inner resistance wire.

On the other hand, an effort to restrain heat generation of the heater to minimize such disadvantages as indicated above, will create another incovenience of insufficient heating of the solid electrolyte while the exhaust gas is low in temperature, or undesired requirement of extra time for heating the solid electrolyte after the start of the engine, before the electromotive force induced by the sensor reaches a level for accurate detection of the oxygen concetration.

The above inconvenience of insufficient heating of the solid electrolyte is serious, particularly when a battery voltage to actuate the heater is low, that is, immediately after the engine is started or while the engine is operated in a cold state. On the contrary, when the battery voltage rises with the engine speed, the temperature of the exhaust gas is elevated. This will aggravate the previously indicated drawback of excessive heating of the solid electrolyte.

Further, a heater used in the traditional oxygen sensor is simply inserted in the hole of a solid electrolyte. That is, no considerations are given to the position of a heating element or resistor such as a resistance wire or coil with respect to the solid electrolyte, for effective and suitable heating of the electrolyte. It is also noted in the art that a relatively large gap is generally provided between the solid electrolyte and the heater so that the ambient air used as reference air may be well circulated in a bore or hole in the solid electrolyte body. Since this gap functions as a thermal barrier to heat transfer from the heater to the solid electrolyte, the heating of the electrolyte tends to be insufficient while the temperature of the exhaust gas is low. Further, an attempt to use a heating element having larger capacity to eliminate this inconvenience will lead to the previously discussed problem of excessive heating of the solid electrolyte when the exhaust gas is heated to an appreciable extent.

SUMMARY OF THE INVENTION

It is accordingly an object of the present invention to provide an improved oxygen sensor having a heater inserted in an elongate bore formed in a body of solid electrolyte, which is durable and reliable in operation even in comparatively varying environmental conditions.

Another object of the invention is to provide such an oxygen sensor having an improved heater which requires less time for sufficient heating of the solid electrolyte even when the temperature of an exhaust gas to be monitored is relatively low, and which protects itself and the solid electrolyte against overheating even when the temperature of the exhaust gas is relatively high.

According to the present invention, there is provided an oxygen sensor comprising: a tubular solid electrolyte body having an elongate bore which is closed at one end of the tubular solid electrolyte body and open at the other end, and further having reference and measuring electrodes on inner and outer surfaces thereof, respectively; a housing which supports or retains the body of solid electrolyte such that the outer surface of the latter is exposed at the closed end to exhaust gas, and such that the elongate bore in the tubular solid electrolyte body of solid electrolyte is held in gas-tight condition with respect to the exhaust gas; and a bar-shaped heater inserted in the elongate bore in the tubular solid electrolyte body. The bar-shaped heater comprises a heating resistor having a positive temperature coefficient of resistance, and a ceramic body carrying the heating resistor so as to embed the heating resistor.

In the oxygen sensor constructed as described above wherein the heating resistor supported and protected by the ceramic body has a positive temperature coefficient, the heater provides a relatively large amount of heat when the temperature of the exhaust gas is comparatively low, but provides a relatively small amount of heat when the exhaust gas temperature is comparatively high, whereby the solid electrolyte is heated to a sufficient level within a short length of time after the start of elevation of the exhaust gas, and the solid electrolyte and the heating resistor are less likely to be overheated even when the sensor is exposed to the exhaust gas of high temperature.

According to one preferred aspect of the invention, the positive temperature coefficient of the heating resistor is not less than 0.3%/°C., so that the principle of the invention is practiced effectively.

In accordance with an advantageous form of the invention, the heating resistor is disposed in a portion of the ceramic body adjacent to a portion of the solid electrolyte body which protrudes out of the supporting housing into the protective tube. In this arrangement, the heating of the solid electrolyte is further optimized.

According to a further advantageous aspect of the invention, a total diametric gap between the heater and the inner surface of the tubular solid electrolyte body is held within a range of 0.3-0.7 mm. This range of the air gap is considered preferable in terms of a compromise between two functional phases of the air gap, i.e., influence of the air gap as a thermal resistor or barrier preventing heat transfer from the heater to the solid electrolyte, on one hand, and role of the air gap as a space for introducing reference gas towards the reference electrode on the inner surface of the solid electrolyte, on the other hand.

In a further advantageous form of the invention, the bar-shaped heater has at least one ventilation passage to permit free circulation of the ambient air in the elongate bore to regularly expose the reference electrode to a fresh volume of the ambient air.

BRIEF DESCRIPTION OF THE DRAWING

The above and other objects, features and advantages of the present invention will be better understood from reading the following description of the preferred embodiments taken in connection with the accompanying drawing in which:

FIG. 1(a) is an elevational view in cross section of one embodiment of an oxygen sensor with a heater of the present invention;

FIG. 1(b) is an enlarged fragmentary view in cross section of a portion A of a tubular solid electrolyte body of the oxygen sensor of FIG. 1(a);

FIG. 2 is a partially sectional schematic illustration of one form of the bar-shaped heater used in the oxygen sensor of FIG. 1(a);

FIG. 3 is a perspective view of one form of a protective metal tube used in the oxygen sensor of FIG. 1(a);

FIG. 4 is a graphical representation of a solid electrolyte temperature in relation to an exhaust gas temperature in the oxygen sensor of the invention, as compared with that in an oxygen sensor known in the art;

FIG. 5 is an elevational view in cross section of another embodiment of the oxygen sensor of the invention;

FIG. 6 is a schematic illustration of a bar-shaped heater used in the oxygen sensor of FIG. 5;

DETAILED DESCRIPTION OF THE PREFERRED EMBODIMENTS

Figure 7:
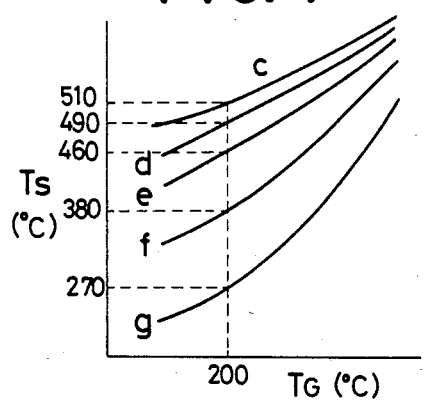
FIG. 7 is a graphical representation of a solid electrolyte temperature in relation to an exhaust gas temperature in oxygen sensors of FIGS. 5 and 6, with their bar-shaped heaters having a heating element (heating resistor) at different positions axially of the heater.

Referring first to FIGS. 1-4, there is illustrated a preferred form of an oxygen sensor embodying the present invention, wherein a tubular solid electrolyte body 1 of solid electrolyte such as zirconia is supported by a housing 2. The tubular solid electrolyte body 1 has an elongate cylindrical bore 1a which is formed longitudinally of the body 1. The elongate bore 1a is closed at one end of the body 1 which is exposed to exhaust gas emitted through an exhaust conduit (not shown), for example, from an internal combustion engine of an automotive vehicle. The elongate bore 1a is open, at the other end of the tubular solid electrolyte body, to ambient atmosphere used as a reference gas. The tubular solid electrolyte solid electrolyte body 1 is provided at its inner and outer surfaces with a reference electrode 1b and a measuring electrode 1c, respectively, as shown in FIG. 1(b), both electrodes 1b and 1c being made of porous platinum (Pt). The tubular solid electrolyte body 1 is retained and sealed in the housing 2, via a talc 3, a metal washer 4 and a metal ring 5, such that the elongate bore 1a is held in gas-tight condition with respect to the exhaust gas, i.e., so that the ambient atmosphere (air) and the exhaust gas do not meet with each other. In the elongate bore 1a, there is inserted a bar-shaped heater 6 to heat the tubular solid electrolyte body 1. The closed end portion of the tubular solid electrolyte body 1 is enclosed by a protective metal tube 7, which protects the closed end portion against direct exposure thereof to a stream of the exhaust gas flowing through the exhaust conduit. The protective metal tube 7 is fixed at its upper end to the lower end of the housing 2, and has flute openings 12 in its peripheral wall to introduce the exhaust gas into the interior of the tube 7 for exposure of the lower or closed end portion of the electrolyte body 1 to the exhaust gas. These flute openings 12 are formed by cutting parts of the peripheral wall and bending these cut parts radially inwardly of the protective metal tube 7 so as to form louver plates 11, as illustrated in FIG. 3.

The bar-shaped heater 6 inserted in the elongate bore 1a of the tubular solid electrolyte body 1 as shown in FIG. 1(a), comprises a ceramic body 8 made of ceramics such as alumina, lead wires 9, and a heating resistor in the form of a resistance wire 10 made of tungsten in this specific example. The lead wires 9 and the heating resistor or resistance wire 10 are carried by the ceramic body 8, more particularly enclosed by or embedded in the mass of the ceramics 8. In the following description, this bar-shaped heater 6 is referred to as "ceramic heater" when appropriate.

The resistance tungsten wire 10 used in this bar-shaped ceramic heater 6 has a positive temperature coefficient of 0.5%/°C. With this selection of the positive temperature coefficient of resistance, the resistance of the tungsten wire 10 is increased and its amount of heat generation is decreased as the temperature of the exhaust gas is elevated, whereby otherwise possible overheating of the solid electrolyte 1 and the heater 7 is prevented at the elevated temperature of the exhaust gas. On the other hand, when the exhaust gas temperature is relatively low, the resistance of the tungsten wire 10 is held low and its amount of heat generation is increased, thereby making it possible to raise the temperature of the solid electrolyte 1 to a level at which an accurate electromotive force is induced by the electrodes 1b, 1c, in a comparatively short time after the start of the vehicle engine in its cold state, or making it possible to heat the solid electrolyte 1 sufficiently while the engine is idling.

A graph of FIG. 4 shows a temperature $T_S$ (°C.) of the solid electrolyte 1 in relation to a temperature $T_G$ (°C.) of the exhaust gas, wherein a curve (a) represents the relation between the temperatures $T_S$ and $T_G$ obtained on the ceramic heater of the instant oxygen sensor, and a curve (b) represents the same relation obtained on a known sheathed heater employing a nichrome wire which is selected so that a length of time from the start of a cold engine to generation of an electromotive force from a sensor using the sheathed heater is substantially equal to that of the oxygen sensor of the invention. At the exhaust temperature of 800° C., the temperature of the solid electrolyte 1 heated by the ceramic heater 6 of the invention is 800° C. as shown by the curve (a), while the temperature of a solid electrolyte heated by the known sheathed heater is 950° C. as indicated by the curve (b). This graph indicates less heating of the electrolyte by the ceramic heater 6 and consequently reduced chance of overheating of the electrolyte when the exhaust temperature $T_G$ is relatively high.

Experiments were conducted, on the oxygen sensor of the invention and the known oxygen sensor used in the measurements of FIG. 4, to check for outlook or appearance of the solid electrolytes and physical condition of the heaters after these sensors are placed in continuous service for 300 hours at an exhaust gas temperature of 800° C. The results on the known sensor showed some cracks of a spinel coating layer which is applied to the outer surface of the solid electrolyte body, and 70% breakage of resistance wire of the sheathed heater. On the oxygen sensor of the invention, neither such cracks nor such breakage were found.

As indicated above, the ceramic heater 6 using the resistance wire 10 having a positive temperature coefficient, has a relatively low level of resistance of the heating element at low exhaust temperatures, and consequently an increased amount of heat generation from the heater, thereby allowing a rapid heating of the solid electrolyte and consequently an earlier generation of an electromotive force from the sensor. This advantage is obtained, for example, immediately after the start of an cold engine, or when the engine is running at its idling speed. On the contrary, a rise of the exhaust temperature to a considerably higher level will cause an appreciable increase in the resistance of the heating element 10. For example, the resistance at 800° C. is approximately five times as high as that at the room temperature. Thus, the possibility of overheating of the solid electrolyte body 1 and the heater 6 is minimized. It is noted that a positive temeprature coefficient of the heating element 10 is important to the heat regulating or controlling performance of the heater 6 as discussed above. In the case where the oxygen sensor is used for an internal combustion engine, it is preferred that the positive temperature coefficient of the heating element 10 be held not less than 0.3%/°C. This coefficient which should be a positive value, is determined by types and/or materials of the heating element or resistor 10, which are specifically selected as needed.

Further, the ceramic body 8 carrying and enclosing the resistance wire 10 assures highly reliable operation of the bar-shaped heater 6 at extremely high temperatures, for a prolonged period of time, even under conditions of frequent thermal shocks.

While the ceramic heater 6 of the present embodiment used the resistance wire 10 embedded in the ceramic body 8, the heating element used according to the invention may be provided in the form of a simple linearly extending wire or a coil wire, as long as it is enclosed by a ceramic material. Further, the resistance wire may be made of metals other than tungsten, such as nickel and platinum, provided the material has a positive temperature coefficient. However, the use of tungsten is particularly recommended for its high heat resistance and durability. The ceramic heater 6 may be fabricated by sintering a formed mass of ceramic powder or slurry with a heating wire embedded in the formed ceramic mass. Further, the ceramic body 8 may be made of commonly knowm ceramics. However, alumina is especially preferred because of its excellent mechanical strength and thermal conductivity.

Referring next to FIGS. 5–9, there is illustrated another preferred embodiment of the oxygen sensor of the invention. The same reference characters as used in FIG. 1(a) will be used in these figures to identify corresponding components.

This embodiment uses a bar-shaped heater 6a which is different from the heater 6 of the preceding embodiment. The bar-shaped heater 6a which is also referred to as ceramic heater, is inserted in the tubular solid electrolyte solid electrolyte body 1, as shown in FIG. 5, such that the heater 6a extends through a center conductor 14 which is press-fitted at its lower end in the upper end of the tubular body 1 and held in pressed contact with the platinum electrode (not shown) to conduct an electromotive force induced by the solid electrolyte.

The bar-shaped ceramic heater 6a comprises; an alumina bar 16; a heating (heat-generating) portion 18 and an electrically conductive portion 20, both formed on the peripheral surface of the alumina bar 16 and connected to each other; and a thin annular sheet of alumina (not shown) wound on the alumina bar 16 to cover the heating and conductive portions 18 and 20. Thus, the alumina bar 16 and the thin annular sheet of alumina constitute a ceramic body carrying the heating and conductive portions 18, 20. The heating and conductive portions 18, 20 are imprints of an electrically resistant material including tungesten as a primary component thereof, which are formed on the surface of the alumina bar 16 by means of printing of the resistant material in a paste state. The alumina bar 16 with the imprints 18, 20 covered with the thin alumina sheet is then baked to form the bar-shaped ceramic heater 16.

The ceramic heater 6a is constructed such that its heating portion 18 is located within a portion of the tubular body 1 (elongate bore 1a) which protrudes by a distance "l" (indicated in FIG. 5) out of the housing 2 into the protective metal tube 7. In other words, the heating portion 18 is disposed on a lower end portion of the alumina bar 16 adjacent the downwardly protruding portion "l" of the tubular solid electrolyte body 1.

This embodiment of the oxygen sensor having the ceramic heater 6a showed a result similar to that indicated by the curve (a) of FIG. 4 obtained in the first embodiment. As previously stated in association with the heating element 10 (resistance wire), the temperature coefficient of the heating portion 18 should preferably be not less than 0.3%/°C. This coefficient of the heating portion 18 may be adjusted as needed, by suitable selection of electrically resistant material used to prepare a paste for printing the heating portion 18 on the alumina bar 16, more specifically by selecting suitable kinds of resistant metal powders, and/or adjusting an amount of glass frits admixed with the metal powders.

Figure 8:
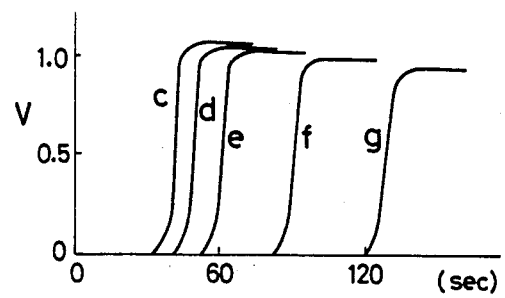
FIG. 8 is also a graphical representation showing a rise of electromotive force induced by the oxygen sensors of FIG. 7, in relation to a running time of an engine started in its cold state.
Figure 9:
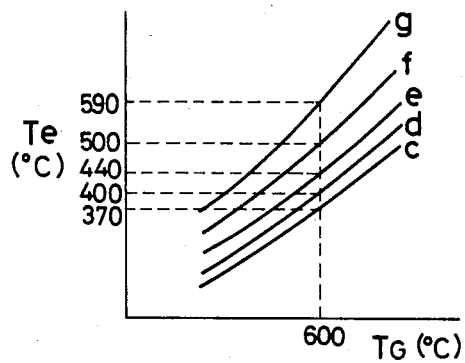
FIG. 9 is a graph illustrating a temperature at the point of contact between a center conductor and the solid electrolyte, in relation to an exhaust gas temperature, in the oxygen sensors of FIGS. 7 and 8.

Referring to FIGS. 7-9, there will be described as to the reasoning why the heating portion 18 should preferably be located within the portion "l" of the solid electrolyte body 1 protruding out of the housing 2.

The tubular body 1 of solid electrolyte is heated by both the exhaust gas introduced through flute openings (not shown in FIG. 5) in the protective metal tube 7, and the bar-shaped ceramic heater 6a. The temperature of the solid electrolyte is raised to some extent by the exhaust gas even when the exhaust temperature is low, that is, during an idling run of an engine or immediately after the start of a cold engine. The temperature rise of the solid electrolyte by the heat of the exhaust gas is highest at the closed end portion "l" of the tubular body 1 which protrudes out of the housing 2.

The efficiency of heating of the solid electrolyte by the heating portion 18 is significantly improved by locating the heating portion 18 within the downwardly protruding portion "l" of the solid electrolyte body 1, for the reasons discussed hereunder. The improvement in the heating efficiency is prominent particularly when the exhaust temperature is relatively low.

Experiments were conducted on the oxygen sensors having the ceramic heaters 6a which are equipped with the heating portion 18 having the same capacity, but disposed at different positions with respect to the tubular body 1. FIG. 7 shows a temperature $T_S$ (°C.) of the solid electrolyte in relation to a temperature $T_g$ (°C.) of the exhaust gas. Curves (c), (d), (e), (f) and (g) respectively represent the temperature relations of the ceramic heaters 6a wherein their heating portions 18 (c)-(g) are respectively located within a portion of the tubular body 1 corresponding to distances of ½l, ¾l, l, 5/4l, and 3/2l, as measured from the lower end of the body 1 (FIG. 5). As illustrated in FIG. 7, the temperature $T_S$ of the solid electrolyte at the exhaust temperature $T_G$ of 200° C. is considerably lower when the heating portions 18(f) and (g) are used, than when the heating portions 18(c), (d) and (e) are used. Stated differently, the upper end of the heating portion 18(e) the entire length of which corresponds to the whole distance "l", is considered to be the critical point for efficient heating of the solid electrolyte. It is presumed that a relatively lower level of the electrolyte temperatures $T_S$ obtained with the heating portions 18(f) and (g) are resultant from easier or more heat transfer from the heating portion 18 to the housing 2 in the case where a portion of the heating portion 18 is located within the housing 2.

Further experiments were conducted on the same sensors 6a as used in the experiments of FIG. 7, to find a rise curve of an electromotive force in relation to a time lapse after the start of a cold engine. The results are represented in FIG. 8 wherein curves (c)-(g) correspond to the curves (c)-(g) of FIG. 7. As depicted in FIG. 8, more time is required before the induced electromotive force has reached a stabilized level, when the heating portions 18(f) and (g) are used. In this respect, the positions of the heating portions (c), (d) and (e) are considered satisfactory. These results suggest that the portion of the tubular solid electrolyte body 1 located within the housing 2 is more difficult to receive heat of the exhaust gas and therefore less likely to be heated in a short time, even with the aid of the heater 6a, to a required level high enough to assure the generation of a stabilized electromotive force from the solid electrolyte. Thus, it is advantageous, for efficient heating of the solid electrolyte, that the heating portion 18 be disposed so as to heat only the closed end portion of the tubular body 1 which protrudes out of the housing 2, i.e., which is located within the protective metal tube 7.

Referring back to FIG. 7, it is noted that a difference in the electrolyte temperature $T_S$ between the curves (c) and (g) at the exhaust temperature $T_G$ of 200° C. was as much as 240° C. A corresponding difference was found to be only 40° C. when the exhaust temperature $T_G$ is 800° C. This finding idicates that the solid electrolyte heated by the heating portion 18(c) is heated to a relatively greater degree when the exhaust gas temperature is relatively low, but not heated so much as to cause overheating of the solid electrolyte body 1 and the heater 6a when the exhaust gas temperature is high. The reason lies in an increased flow of the exhaust gas as its temperature is elevated. In other words, a comparatively large volume of the exhaust gas will contribute to cooling of the solid electrolyte.

Further experiments were conducted on the same oxygen sensors 6a to find a temperature Te (°C.) at the point of contact between the solid electrolyte body 1 and the center conductor 14, in relation to the exhaust temperature $T_G$ (°C.). The results are shown in FIG. 9 wherein curves (c)-(g) correspond to the curves (c)-(g) of FIGS. 7 and 8. The graph of FIG. 9 indicates that the temperature Te is elevated to a greater degree when the heater 6a is equipped with the heating portion 18(f) or (g). In this connection, it is preferred that the temperature at the interface between the conductor 14 and the solid electrolyte 1 be held as low as possible, for enhanced reliability of contact therebetween.

An overall analysis of the experiments which have been discussed dictates that the heating portion 18 of the bar-shaped ceramic heater 6a be located within the closed end portion of the tubular solid electrolyte body 1 which protrudes out of the housing 2, preferably within the range of three-fourths of the protruding distance, as measured from the closed end.

In summary, the oxygen sensor of this modified embodiment of FIGS. 5 and 6 is characterized by the bar-shaped heater 6a the heating portion of which is located within the closed end portion of the tubular body 1 protruding from the housing 2. This feature contributes to enhancement in the heating efficiency: sufficient heating of the solid electrolyte at low exhaust temperatures; shortened time between the start of a cold engine and the generation of an electromotive force from the sensor; and reduced chance of overheating of the electrolyte and the heater at high exhaust temperatures, all combining to assure improved reliability in controlling an air-fuel ratio of an engine.

The bar-shaped heaters 6 of the first embodiment of FIGS. 1-2 and 6a of the above modified embodiment of FIGS. 5-6 are both disposed in the elongate bore 1a such that there exits a radial gap or clearance of 0.5 mm (in diameter: hereinafter called "total diametric gap") with respect to the inner surface of the tubular body 1 which defines the elongate bore 1a. However, this total diametric gap between the opposite surfaces of the heater 6, 6a and the electrolyte body 1 must be held within the range of 0.3-0.7 mm for the reasons stated below.

In general, the assembling of a bar-shaped heater and a tubular solid electrolyte body is made easier as a larger gap is provided between the outer surface (outside diameter) of the heater and the opposite inner surface of the tubular solid electrolyte body. However, the increased gap means an increase in the volume of an annular space serving as a thermal resistor between the two members. Hence, the efficiency of heating the solid electrolyte by the heater is decreased as the gap therebetween is increased, provided the heating capacity of the heater is constant. Thus, an excessive gap between the two members will lead to insufficient heating of the solid electrolyte, and unstable electromotive force of the electrolyte when an exhaust gas temperature of an engine is low, or result in increased time after the start of a cold engine for obtaining an electromotive force accurately representing the oxygen concentration of the exhaust gas. On the other hand, an increase in the heating capacity of the bar-shaped heater to solve the above problem of insufficient heating will cause another problem of excessive heating of the solid electrolyte and the heater itself when the exahust temperature is elevated, whereby the life of the heater and platinum electrodes on the solid electrolyte body is reduced.

The excessive gap between the heater and the solid electrolyte increases the possibility of radial misalignment, i.e., an error in concentricity of the bar-shaped heater with respect to the elongate bore in the electrolyte body. Described more specifically, a misaligned heater has a circumferential portion very close to the inner surface of the solid electrolyte, and another circumferential portion relatively distant from the inner surface, whereby the solid electroltye is subject to local overheating by the heater at high exhaust temperatures, leading to deterioration or degradation of the platinum electrode, while the circumferential portion of the solid electrolyte distant from the heater is not heated satisfactorily when the exhaust temperature is low.

As indicated above, a relatively small gap between the bar-shaped heater and the tubular solid electrolyte body is considered to permit relatively sufficient heating of the solid electrolyte with a comparatively small amount of heat, and contribute to less chance of overheating of the sensor at high exhaust temperatures. With the above factors and the deterioration of the solid electrolyte and the heater taken into consideration, the total diametric gap (clearance in diameter) in question should preferably be not greater than 0.7 mm.

In the meantime, the diametric gap should be not less than 0.3 mm. With the gap smaller than 0.3 mm, the ambient reference air is not expected to circulate satisfactorily in the elongate bore in the electrolyte body. Accordingly, in the event of entry of any foreign gas into the elongate bore (gap) and consequent change in the reference oxygen concentration within the bore, an extremely long period of time is required before such an foreign gas is exhausted. This causes the oxygen sensor to produce an inaccurate electromotive force.

Figure 10:
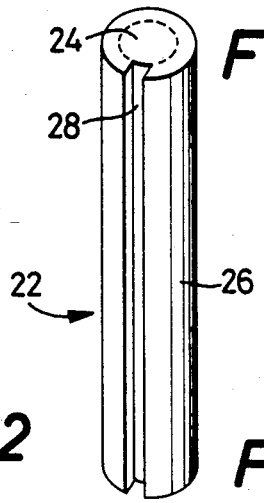
FIG. 10 is a perspective view of a modified form of a bar-shaped heater used in the present oxygen sensor in place of the heaters of FIGS. 2 and 6.

While the two different forms of the bar-shaped heaters 6 and 6a have been described in connection with the foregoing embodiments of the invention, these heaters 6, 6a may be replaced by a bar-shaped heater generally indicated at 22 in FIG. 10. This bar-shaped heater 22 is made from a ceramic bar 24 and a ceramic sheet 26, both being formed of a suitable ceramic material such as alumina. In forming the heater 22, a paste of electrically resistant material including tungsten, for example, is prepared to print patterns of a heating portion (not shown) and an electrically conductive portion (not shown) on one surface of the ceramic sheet 26. This ceramic sheet 26 is then wound on the ceramic bar 24 such that the printed surface of the sheet 26 is held in contact with the surface of the bar 24. The dimensions of the ceramic bar and sheet 24, 26 are so determined that the entire periphery of the ceramic bar 24 is not covered or enclosed by the ceramic sheet 26, i.e., the opposite ends of the wound sheet 26 are spaced a slight distance from each other circumferentially of the ceramic bar 24 so that a groove 28 is formed as a ventilation passage extending along the length of the heater 22.

The ventilation groove 28 serves to facilitate free circulation of ambient air in the elongate bore 6, 6a to expose the reference electrode regularly to a fresh volume of a reference gas such as the ambient air, whereby the reference oxygen concentration within the tubular solid electrolyte body 1 is kept constant for a long period of service of the oxygen sensor. A further advantage offered by the ventilation groove 28, is the possibility of reducing the previously indicated gap or clearance of the heater with respect to the solid electrolyte. Stated the other way, the provision of the groove 28 allows the heater 22 to be placed very close to the inner surface of the tubular body 1. In this instance, the solid electrolyte may be heated efficiently with a relatively small amount of heat even at low exhaust temperatures, while on the other hand, the ventilation groove 28 prevents otherwise possible overheating of the sensor at high exhaust temperatures.

The ventilation groove 28 also serves to rapidly exhaust a foreign gas which may possiblly enters the solid electrolyte body 1 for some reasons and change the oxygen concentration of the ambient reference air.

Figure 11:
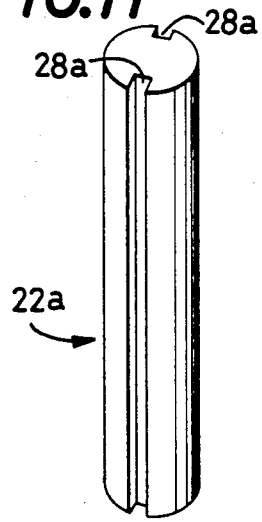
FIGS. 11, 12 and 13 are perspective view of alternative forms of the bar-shaped heater used in place of the heater of FIG. 10.
Figure 12:
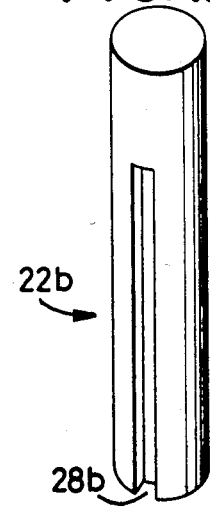
Figure 13:
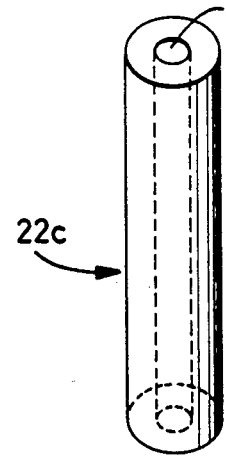

The ventilation groove 28 may be replaced by other forms of passages as shown in FIGS. 11-13. In a ceramic heater 22a of FIG. 11, a pair of ventilation grooves 28a are formed in diametrically opposite peripheral portions, along the entire length of the heater 22a. A ceramic heater 22b of FIG. 12 has a ventilation groove 28b which is formed along a part of the entire length of the heater 22b. In this case, the length of the groove 28b is determined just to meet the minimum requirement of holding the elongate bore 1a in communication with the ambient atmosphere. A heater 22c of FIG. 13 has a ventilation bore 28c which is formed through its radially central part. Further, as suggested in FIG. 11, it is apparent to provide plural ventilation passages at suitable positions in the heater.

In the case where any number of ventilation passages are provided in any form, a total cross sectional area of the passage or passages should be not less than 0.1 mm$^2$, preferably not less than 0.3 mm$^2$. Further, it is preferred that the ventilation groove or grooves be dimensionsed so that a total circumferential area of the heater in which the groove or grooves are formed, will not be greater than one-third of the entire circumferential surface area of the heater.

While the present invention has been described in its preferred embodiments, it is to be understood that the invention is not limited thereto but may be otherwise embodied within the scope of the appended claims.

What is claimed is:

1. An oxygen sensor comprising:
  a tubular solid electrolyte body having an elongate bore therein, a first end of said elongate bore is closed by one end of said tubular solid electrolyte body and a second end of said elongate bore is open at a second end of said tubular solid electrolyte body, said tubular body having reference and measuring electrodes on inner and outer surfaces thereof, respectively;
  a housing body which supports said tubular solid electrolyte body such that said outer surface of said tubular body is exposed at said one end of said tubular body to an exhaust gas, said housing body maintaining said elongate bore in a gas-tight condition with respect to said exhaust gas and said one end of said tubular body extends outwardly from said housing body; and
  a bar-shaped heater inserted in said elongate bore of said tubular solid electrolyte body, and comprising a resistance heating portion having a positive temperature coefficient of resistance of not less than 0.3%/°C.,
and a ceramic body carrying said resistance heating portion, the resistance heating portion being located only in said one end of the tubular body which extends outwardly from the housing body and not extending past said housing body.

2. An oxygen sensor as recited in claim 1, wherein said bar-shaped heater comprises a bar-shaped mass of alumina and a resistance wire embedded in said mass of alumina.

3. An oxygen sensor as recited in claim 2, wherein said resistance wire is made of tungsten.

4. An oxygen sensor as recited in claim 1, wherein said bar-shaped heater comprises a first mass of alumina, a second mass of alumina cooperating with said first mass of alumina to form said ceramic body, and an imprint of an electrically resistant material carried on a mating between said first and second masses of alumina.

5. An oxygen sensor as recited in claim 4, wherein said electrically resistant material includes tungsten as a primary component thereof.

6. An oxygen sensor as recited in claim 1, wherein said bar-shaped heater is disposed in said elongate bore with a total diametric gap of 0.3–0.7 mm with respect to said inner surface of said tubular solid electrolyte body.

7. An oxygen sensor as recited in claim 1, wherein said bar-shaped heater has at least one ventilation passage for free circulation of ambient air in said elongate bore to expose said reference electrode to a fresh volume of the ambient air.

8. An oxygen sensor as recited in claim 7, wherein said ventilation passage is a groove formed in an outer peripheral surface of said bar-shaped heater along a longitudinal length thereof.

9. An oxygen sensor as recited in claim 8, wherein bar-shaped heater in which said at least one ventilation passage occupies not greater than one-third of an entire circumferential area of said bar-shaped heater.

10. An oxygen sensor as recited in claim 7, wherein said ventilation passage is a bore formed through a radially central part of said bar-shaped heater.

11. An oxygen sensor as recited in claim 1, wherein said at least one ventilation passage has a total cross sectional area of not less than 0.1 mm$^2$.

12. An oxygen sensor as recited in claim 1, further comprising a protective tube made of metal and enclosing an end portion of said tubular solid electrolyte body adjacent said one end thereof and having an opening for introducing said exhaust gas into said protective tube for exposure of said one end of the tubular solid electrolyte body to said exhaust gas.

13. An oxygen sensor as recited in claim 1, wherein said reference and measuring electrodes are made of porous platinum.

14. An oxygen sensor comprising:
  a tubular solid electrolyte body having an elongate bore therein, a first end of said elongate bore is closed by one end of said tubular solid electrolyte body and a second end of said elongate bore is open at a second end of said tubular solid electrolyte body, said tubular body having reference and measuring electrodes on inner and outer surfaces thereof, respectively;
  a housing body which supports said tubular solid electrolyte body such that said outer surface of said tubular body is exposed at said one end of said tubular body to an exhaust gas, said housing body maintaining said elongate bore in a gas-tight condition with respect to said exhaust gas and said one end of said tubular body extends outwardly from said housing body; and
  a bar-shaped heater inserted in said elongate bore of said tubular solid electrolyte body, and comprising a resistance heating portion having a positive temperature coefficient of resistance of not less than 0.3%/°C. and a ceramic body carrying said resistance heating portion so as to embed the resistance heating portion therein, the resistance heating portion being located only in said one end of the tubular body which extends outwardly from the housing body and not extending past said housing body.

15. An oxygen sensor comprising:
  a tubular solid electrolyte body having an elongate bore therein, a first end of said elongate bore is closed by one end of said tubular solid electrolyte body and a second end of said elongate bore is open at a second end of said tubular solid electrolyte body, said tubular body having reference and measuring electrodes on inner and outer surfaces thereof, respectively;
  a housing body which supports said tubular solid electrolyte body such that said outer surface of said tubular body is exposed at said one end of said tubular body to an exhaust gas, said housing body maintaining said elongate bore in a gas-tight condition with respect to said exhaust gas and said one end of said tubular body extends outwardly from said housing body;

a protective cylindrical member enclosing said ene end of the tubular solid electrolyte body, said protective cylindrical member having at least one opening to permit said exhaust gas to be in contact with said one end of said tubular body; and a bar-shaped heater inserted in said elongate bore of said tubular solid electrolyte body, and comprising a resistance heating portion having a positive temperature coefficient of resistance of not less than 0.3%/°C. and a ceramic body carrying said resistance heating portion, the resistance heating portion being located only in said one end of the tubular body and extending only within the protective cylindrical member enclosing said one end of said tubular solid electrolyte body.

* * * * *